United States Patent
Matsuda et al.

[11] Patent Number: 6,013,748
[45] Date of Patent: Jan. 11, 2000

[54] AROMATIC ESTER COMPOUND AND SECOND-ORDER NON-LINEAR OPTICAL MATERIAL THEREWITH

[75] Inventors: Hiroo Matsuda; Takashi Fukuda; Shinji Yamada, all of Tsukuba; Tatsumi Kimura, Nagareyama; Masao Kato, Tsukuba; Xuan-Ming Duan, Sendai; Shuji Okada, Sendai; Hachiro Nakanishi, Sendai, all of Japan

[73] Assignee: Japan as represented by Director General of Agency of Industrial Science and Technology, Japan

[21] Appl. No.: 09/046,658

[22] Filed: Mar. 24, 1998

[30] Foreign Application Priority Data

May 8, 1997 [JP] Japan .................................. 9-134315

[51] Int. Cl.[7] ...................................................... C08F 2/00
[52] U.S. Cl. ......................... 526/213; 526/215; 521/180; 560/72
[58] Field of Search .............................. 560/72; 521/180; 526/213, 215

[56] References Cited

FOREIGN PATENT DOCUMENTS 2937911  3/1980  Germany .

*Primary Examiner*—Paul J. Killos
*Attorney, Agent, or Firm*—Wenderoth, Lind & Ponack, L.L.P.

[57] ABSTRACT

Disclosed is a novel aromatic ester compound represented by the general formula

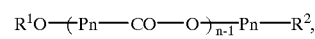

in which Pn is a 1,4-phenylene group, $R^1$ is an alkyl group having 1 to 4 carbon atoms, $R^2$ is a group selected from the group consisting of perfluoroalkyl groups having 1 to 4 carbon atoms, cyano group, nitro group, 2,2-dicyanoethenyl group and methylsulfonyl group and the subscript n is a number of 2, 3 or 4. These aromatic ester compounds are useful as a second-order non-linear optical material in the ultraviolet wavelength range so that a resin film containing the compound has a good second-order non-linear optical coefficient $d_{33}$ of $2$–$4 \times 10^{-9}$ esu.

2 Claims, 1 Drawing Sheet

FIGURE
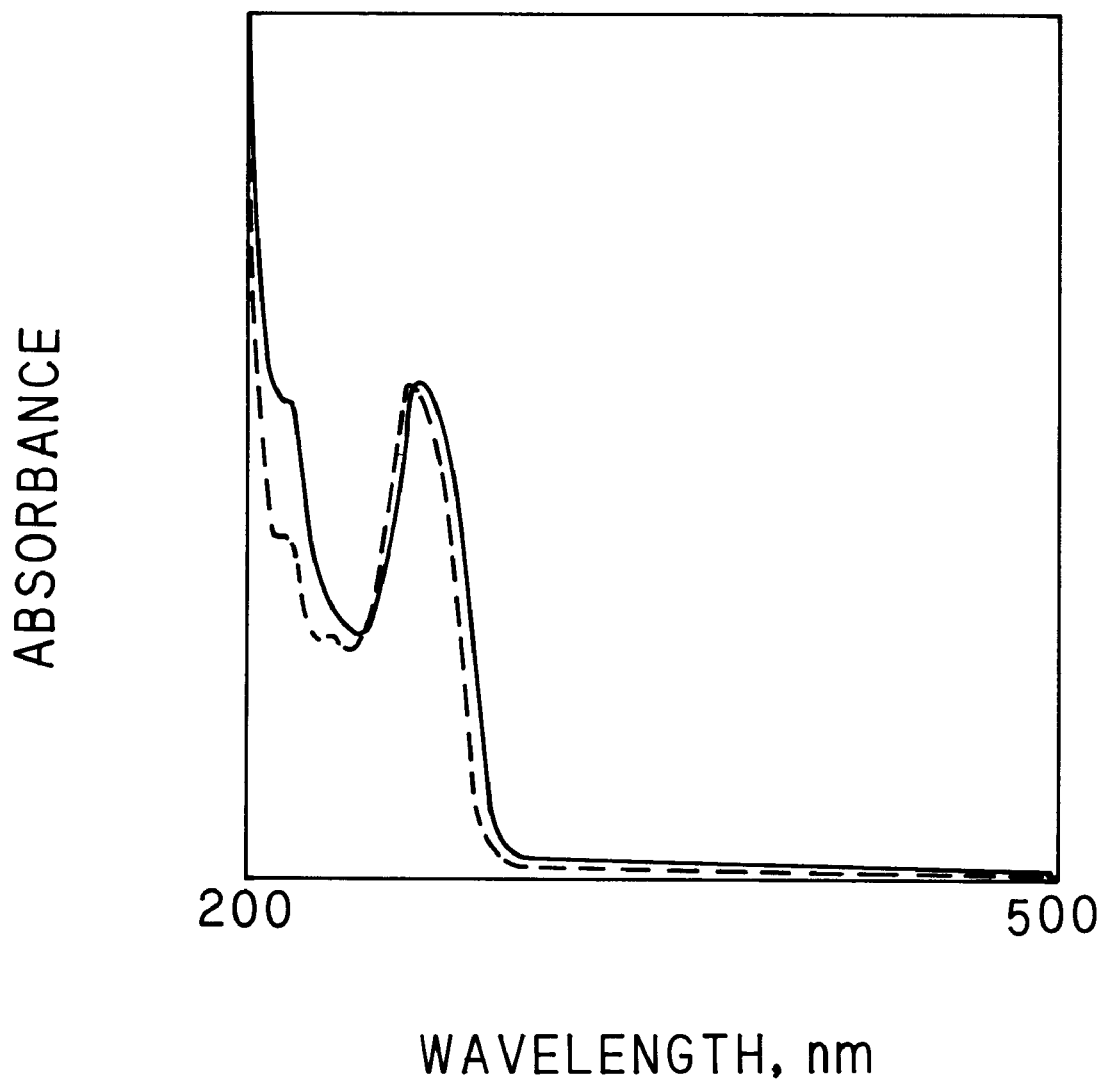

AROMATIC ESTER COMPOUND AND SECOND-ORDER NON-LINEAR OPTICAL MATERIAL THEREWITH

BACKGROUND OF THE INVENTION

The present invention relates to a novel aromatic ester compound capable of exhibiting a second-order non-linear optical characteristic and a second-order non-linear optical material therewith.

It will be very essential in the coming highly information-predominant society in the near future to develop a highly efficient information-transmitting means by which a large amount of information of high precision can be transferred at a very high speed and in a high density. The optical technology is, along with the electronic technology in supplementation each to the other, expected to play a fundamentally important role in this technological field of information transmission by virtue of the unique and excellent characteristics of parallelism, space processability, adaptability to information processing of a large quantity and capability of high-density information transmission. In these days, several kinds of organic non-linear optical materials have come under highlight as a class of materials satisfying the requirements in the information transmission technology by optical means.

In contrast to the non-linear effect exhibited by the inorganic materials as reported heretofore, which is due to the absorption of lattice vibration, the non-linear effect exhibited by organic materials is due to the dipole moment produced as a result of the distortion in the π-electron system by the substituent groups inherently without being accompanied by the lattice vibration enabling a high-speed response.

A second-order non-linear optical material is required to have high optical transparency and large non-linear optical characteristic. As a class of the second-order non-linear optical materials satisfying these requirements, attention is directed in recent years toward the so-called chained-chromophore organic non-linear optical materials. A chained-chromophore organic non-linear optical material here implied is an organic material developed under a concept that the value of $\mu\beta$, which is one of the characteristic parameters of second-order non-linear optical materials, is increased in proportion to the square of the number of units when non-linear active units are linearly combined together. Examples of known chained-chromophore organic non-linear optical materials include aromatic ester compounds and oligomers of an aromatic ester compound but these aromatic ester-based compounds, though having satisfactorily high transparency, are not very satisfactory in respect of the non-linear optical characteristics.

The second-order optical characteristic of a substance is a phenomenon which can be exhibited only when the substance lacks a center of symmetry. In polymeric materials, such a structure is obtained usually by the application of an electric field to the material to cause uniaxial orientation of the non-linear active species and a higher degree of the orientation results in greater performance of the material. One of the factors which greatly influence the degree of orientation is the dipole moment possessed by the molecules. The dipole moment of conventional aromatic ester compounds and oligomers of an aromatic ester compound, however, is not so large as compared with that of non-linear active species in general so that a high degree of orientation can hardly be obtained and, as a result, the second-order non-linear optical characteristic cannot be obtained or, even if it be obtained, cannot be high enough.

SUMMARY OF THE INVENTION

The present invention accordingly has an object, under the above described situations in the prior art, to provide a novel aromatic ester compound having high optical transparency and capable of exhibiting excellent second-order non-linear optical characteristics.

Thus, the present invention provides a second-order non-linear optical material which is an aromatic ester compound represented by the general formula

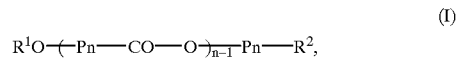
(I)

in which Pn is a 1,4-phenylene group, $R^1$ is an alkyl group having 1 to 4 carbon atoms, $R^2$ is a group selected from the group consisting of perfluoroalkyl groups, cyano group, nitro group, 2,2-dicyanoethenyl group and methylsulfonyl group and the subscript n is a number of 2, 3 or 4.

BRIEF DESCRIPTION OF THE DRAWING

The FIGURE shows the ultraviolet absorption spectra of the aromatic ester compound prepared in Example 1 in the form of a solution and in the form of a thin film.

DETAILED DESCRIPTION OF THE PREFERRED EMBODIMENTS

The aromatic ester compound capable of exhibiting a second-order non-linear optical characteristic provided by the present invention is a novel compound having a structure represented by the above given general formula (I). In the formula, the group denoted by $R^1$ is an alkyl group having 1 to 4 carbon atoms exemplified by methyl, ethyl, n-propyl, isopropyl, n-butyl, isobutyl, sec-butyl and tert-butyl groups, of which methyl group is particularly preferred in respect of the high second-order non-linear optical characteristic of the aromatic ester compound. The group denoted by $R^2$ is, as is defined above, a group selected from the group consisting of perfluoroalkyl groups, cyano group, nitro group, 2,2-dicyanoethenyl group and methylsulfonyl group. Among the perfluoroalkyl groups, particularly preferred are those having 1 to 4 carbon atoms such as trifluoromethyl and pentafluoroethyl groups, of which trifluoromethyl group is more preferable in respect of the high second-order non-linear optical characteristic exhibited by the aromatic ester compound. The subscript n is a number of 2, 3 or 4. Although the number of n should be as large as possible in order to obtain higher second-order non-linear optical characteristics exhibited by the aromatic ester compound, an aromatic ester compound of the general formula (I) in which the value of n is 5 or larger can be synthesized only with undue troublesomeness rendering use thereof as a second-order non-linear optical material almost impractical.

While the aromatic ester compounds represented by the general formula (I) in general have high optical transparency, particularly preferable compounds among them from the standpoint of obtaining excellent second-order non-linear optical characteristics include:

4-cyanophenyl 4-anisate, referred to as E2-CN hereinafter, expressed by the structural formula

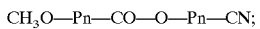

4-cyanophenyl 4-(4'-methoxyphenylcarbonyloxy) benzoate, referred to as E3-CN hereinafter, expressed by the structural formula CH₃O—Pn—CO—O—Pn—CO—O—Pn—CN;

4-trifluoromethylphenyl 4-anisate, referred to as E2-CF₃ hereinafter, expressed by the structural formula CH₃O—Pn—CO—O—Pn—CF₃;

4-trifluoromethylphenyl 4-(4'-methoxyphenylcarbonyloxy) benzoate, referred to as E3-CF₃ hereinafter, expressed by the structural formula CH₃O—Pn—CO—O—Pn—CO—O—Pn—CF₃; and 4-nitrophenyl 4-anisate, referred to as E2-NO₂ hereinafter, expressed by the structural formula CH₃O—Pn—CO—O—Pn—NO₂.

As is mentioned above, the novel aromatic ester compounds represented by the general formula (I) in general have good optical transparency and are capable of exhibiting high second-order non-linear optical characteristics. For example, a thin film of a polymethyl methacrylate resin having a thickness of about 500 nm and containing 10% by weight of the inventive aromatic ester compound dispersed therein has second-order non-linear optical characteristics that the optimum poling temperature is in the range from 60 to 90° C. and the second-order non-linear optical coefficient $d_{33}$ value of the resin film, after a poling treatment at a temperature in this range, is in the range from $2 \times 10^{-9}$ to $4 \times 10^{-9}$ esu.

While the inventive aromatic ester compound of the general formula (I) can be prepared by various synthetic routes, following is a description of typical synthetic procedures (a), (b) and (c) each applicable to the compounds having different values of n, by which the inventive aromatic ester compound can be easily prepared.

(a) The aromatic ester compound of the general formula (I), of which $R^2$ is a perfluoroalkyl, cyano, nitro, 2,2-dicyanoethenyl or methylsulfonyl group and the value of n is 2, is prepared by the following synthetic route.

The synthetic procedure can be expressed by the following reaction scheme:

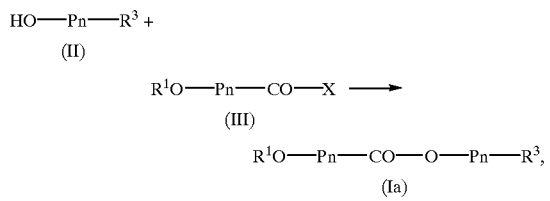

in which $R^3$ is a perfluoroalkyl, cyano, nitro, 2,2-dicyanoethenyl or methylsulfonyl group, X is a halogen atom and $R^1$ and Pn each have the same meaning as defined before.

Thus, the compound (II) and the compound (III) are dissolved in a suitable organic solvent such as acetone containing an acceptor of hydrogen halide such as triethylamine in a substantially stoichiometric proportion so that the dehydrohalogenating esterification reaction proceeds in the solution even without heating to give the compound (Ia).

(b) The aromatic ester compound of the general formula (I), of which $R^2$ is a perfluoroalkyl, cyano, nitro, 2,2-dicyanoethenyl or methylsulfonyl group and the value of n is 3, is prepared by the following synthetic route.

The synthetic procedure can be expressed by the following reaction scheme:

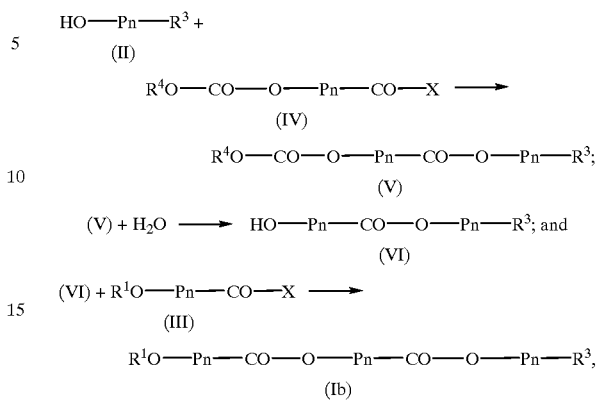

in which $R^4$ is an alkyl group having 1 to 4 carbon atoms and the other symbols each have the same meaning as defined before.

Thus, the compound (II) and the compound (IV) are dissolved in a suitable organic solvent such as acetone containing an acceptor of hydrogen halide such as triethylamine in a substantially stoichiometric proportion so that the dehydrohalogenating esterification reaction proceeds in the solution even without heating to give the compound (V).

In the next place, the compound (V) is dissolved in a suitable organic solvent such as acetone containing a basic catalyst and subjected to a hydrolysis reaction to give the compound (VI), which is reacted with the compound (III) to effect a second esterification reaction in a similar manner to that in the synthetic procedure (a) described above to give the oligomeric aromatic ester compound (Ib).

(c) The aromatic ester compound of the general formula (I), of which $R^2$ is a perfluoroalkyl, cyano, nitro, 2,2-dicyanoethenyl or methyl sulfonyl group and the value of n is 4, is prepared by the following synthetic route.

The synthetic procedure can be expressed by the following reaction scheme with the compounds (VI) and (IV) defined above as the starting reactants:

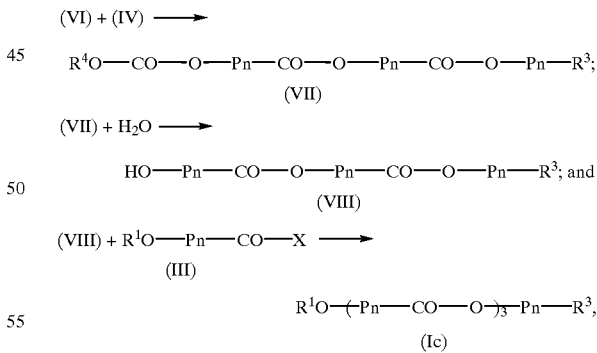

in which each of the symbols has the same meaning as defined above.

Thus, the compound (VI) obtained in the same manner as in the procedure (b) described above and the compound (IV) are dissolved in a suitable organic solvent such as acetone containing an acceptor of hydrogen halide such as triethylamine in a substantially stoichiometric proportion so that the dehydrohalogenating esterification reaction proceeds in the solution even without heating to give the compound (VII).

In the next place, the compound (VII) is dissolved in a suitable organic solvent such as acetone containing a basic catalyst and subjected to a hydrolysis reaction to give the compound (VIII), which is reacted with the compound (III) in the same manner as in the procedure (a) to effect a second esterification reaction giving the desired oligomeric aromatic ester compound (Ic).

In the following, the present invention is described in more detail by way of Examples.

EXAMPLE 1

The aromatic ester compound E2-CN was synthesized in the following manner. Thus, a reaction mixture was prepared by dissolving 3.68 g (30.9 mmoles) of 4-cyanophenol and 4.3 ml (31 mmoles) of triethylamine in 20 ml of acetone with agitation under chilling in an ice bath. In the next place, 5.60 g (32.8 mmoles) of p-anisoyl chloride were added dropwise to the reaction mixture over a period of 15 minutes followed by further continued agitation of the mixture kept in the ice bath as such overnight to effect the reaction.

After completion of the reaction, the reaction mixture was admixed with methylene chloride and the organic solution was washed with water and then freed from the solvents by distillation to give a white solid product, which was purified by recrystallization from a mixture of methyl alcohol and water to give 7.17 g of a white acicular crystalline product having a melting point of 109.9–110.3° C. This product could be identified to be the desired aromatic ester compound E2-CN from the results of the $^1$H-NMR spectrometric structure analysis shown below. The yield of the reaction product was 91.6% of the theoretical value.

$^1$H-NMR (CDCl$_3$, δ, ppm): 3.91 (s, 3H, CH$_3$—O—Ph—); 7.00 (d, J=8.8 Hz, 2H, aromatic protons); 7.36 (d, J=9.2 Hz, 2H, aromatic protons); 7.74 (d, J=8.4 Hz, 2H, aromatic protons); and 8.14 (d, J=8.8 Hz, 2H, aromatic protons)

FIG. 1 of the accompanying drawing shows the ultraviolet absorption spectra of the thus prepared aromatic ester compound in the form of a solution in acetonitrile and in the form of a thin film by the broken line curve and solid line curve, respectively.

The wavelength for the absorption maximum $\lambda_{max}$ and the cut-off wavelength $\lambda_{co}$ of the compound E2-CN determined from the ultraviolet absorption spectrum of the acetonitrile solution were 262 nm and 298 nm, respectively.

EXAMPLE 2

The aromatic ester compound E3-CN was synthesized in the following manner. Thus, in the first step, a reaction mixture was prepared by dissolving 2.20 g (18.5 mmoles) of 4-cyanophenol and 2.6 ml (19 mmoles) of triethylamine in 15 ml of acetone with agitation under chilling in an ice bath. In the next place, a solution of 4.23 g (18.5 mmoles) of 4-ethoxycarbonyloxy benzoyl chloride dissolved in 15 ml of acetone was added dropwise to the reaction mixture over a period of 15 minutes followed by further continued agitation of the mixture kept in the ice bath as such overnight to effect the reaction.

After completion of the reaction, the reaction mixture was admixed with methylene chloride and the organic solution was washed with water and then freed from the solvents by distillation to give a solid product, which was purified by recrystallization from methyl alcohol to give 4.44 g of a light brown solid product. This product could be identified to be 4-cyanophenyl 4-ethoxycarbonyloxy benzoate from the results of the $^1$H-NMR spectrometric structure analysis shown below. The yield of the reaction product was 77.1% of the theoretical value.

$^1$H-NMR (CDCl$_3$, δ, ppm): 1.42 (t, J=7.0 Hz, 3H, CH$_3$CH$_2$—O—CO—O—); 4.36 (q, J=7.2 Hz, 2H, CH$_3$CH$_2$—O—CO—O—); 7.37 (m, 4H, aromatic protons); 7.75 (d, J=8.8 Hz, 2H, aromatic protons); and 8.23 (d, J=8.4 Hz, 2H, aromatic protons)

In the second step, 3.00 g (9.63 mmoles) of the 4-cyanophenyl ester compound obtained in the first step were dissolved in a mixture of 17 ml of pyridine, 35 ml of acetone and 2.0 ml of 28% ammonia water and kept overnight under agitation to effect the hydrolysis reaction. After completion of the reaction, the reaction mixture was admixed with methylene chloride and the organic solution was washed first with 1N hydrochloric acid and then with water followed by removal of the solvents by distillation to give a solid product which was purified by recrystallization from a mixture of methyl alcohol and water to give 0.92 g of a slightly brownish, white crystalline material as the product. This product could be identified to be 4-cyanophenyl 4-hydroxybenzoate from the results of the $^1$H-NMR spectrometric structure analysis shown below. The yield of this reaction product was 39.9% of the theoretical value.

$^1$H-NMR (CDCl$_3$, δ, ppm): 5.43 (s, broad, 1H, HO—Ph—); 6.94 (d, J=8.8 Hz, 2H, aromatic protons); 7.35 (d, J=8.8 Hz, 2H, aromatic protons); 7.74 (d, J=8.8 Hz, 2H, aromatic protons); and 8.11 (d, J=8.8 Hz, 2H, aromatic protons)

In the third step, 0.90 g (3.8 mmoles) of the 4-cyanophenyl 4-hydroxybenzoate prepared above was dissolved in a mixture of 0.6 ml (4 mmoles) of triethylamine and 20 ml of acetone with agitation under chilling in an ice bath to prepare a reaction mixture to which 0.64 g (3.8 mmoles) of p-anisoyl chloride was added dropwise over a period of 15 minutes followed by further continued agitation of the reaction mixture overnight in the ice bath as such to effect the esterification reaction. After completion of the reaction, the reaction mixture was admixed with methylene chloride and the organic solution was washed with water and then freed from the solvents by distillation to give a solid material which was purified by recrystallization from acetone to give 1.26 g of a white crystalline product. This product could be identified to be the desired aromatic ester compound E3-CN from the results of the $^1$H-NMR spectrometric structure analysis shown below. The yield of the reaction product was 89.7% of the theoretical value.

$^1$H-NMR (CDCl$_3$, δ, ppm): 3.92 (s, 3H, CH$_3$—O—Ph—); 7.01 (d, J=8.0 Hz, 2H, aromatic protons); 7.39 (m, 4H, aromatic protons); 7.76 (d, J=8.0 Hz, 2H, aromatic protons); 8.17 (d, J=8.0 Hz, 2H, aromatic protons); and 8.27 (d, J=8.0 Hz, 2H, aromatic protons)

The wavelength for the absorption maximum $\lambda_{max}$ and the cut-off wavelength $\lambda_{co}$ of the compound E3-CN determined from the ultraviolet absorption spectrum of an acetonitrile solution were 263 nm and 298 nm, respectively.

EXAMPLE 3

The aromatic ester compound E2-CF$_3$ was synthesized in the following manner. Thus, a reaction mixture was prepared by dissolving 5.00 g (30.9 mmoles) of 4-trifluoromethyl phenol and 4.3 ml (31 mmoles) of triethylamine in 15 ml of acetone with agitation under chilling in an ice bath. In the next place, a solution of 5.27 g (30.9 mmoles) of p-anisoyl chloride dissolved in 10 ml of acetone was added dropwise to the reaction mixture over a period of 15 minutes followed by further continued agitation of the mixture kept in the ice bath as such overnight to effect the reaction.

After completion of the reaction, the reaction mixture was admixed with methylene chloride and the organic solution was washed with water and then freed from the solvents by distillation to give a solid product, which was purified by recrystallization from a mixture of methyl alcohol and water to give 2.8 g of a white crystalline product having a melting point of 101.3–101.7° C. This product which could be identified to be the desired aromatic ester compound E2-$CF_3$ from the results of the $^1$H-NMR spectrometric structure analysis shown below. The yield of the reaction product was 70.0% of the theoretical value.

$^1$H-NMR (CDCl$_3$, δ, ppm): 3.91 (s, 3H, $\underline{CH_3}$—O—Ph—); 7.00 (d, J=8.8 Hz, 2H, aromatic protons); $\overline{7.34}$ (d, J=8.8 Hz, 2H, aromatic protons); 7.70 (d, J=8.4 Hz, 2H, aromatic protons); and 8.16 (d, J=8.8 Hz, 2H, aromatic protons)

The wavelength for the absorption maximum $\lambda_{max}$ and the cut-off wavelength $\lambda_{co}$ of the compound E2-$CF_3$ determined from the ultraviolet absorption spectrum of an acetonitrile solution were 261 nm and 295 nm, respectively.

EXAMPLE 4

The aromatic ester compound E3-$CF_3$ was synthesized in the following manner. Thus, in the first step, a reaction mixture was prepared by dissolving 3.00 g (18.5 mmoles) of 4-trifluoromethyl phenol and 2.6 ml (19 mmoles) of triethylamine in 20 ml of acetone with agitation under chilling in an ice bath. In the next place, a solution of 4.23 g (18.5 mmoles) of 4-ethoxycarbonyloxy benzoyl chloride dissolved in 20 ml of acetone was added dropwise to the reaction mixture over a period of 15 minutes followed by further continued agitation of the mixture kept in the ice bath as such overnight to effect the reaction.

After completion of the reaction, the reaction mixture was admixed with methylene chloride and the organic solution was washed with water and then freed from the solvents by distillation to give a solid product, which was purified by recrystallization from a mixture of methyl alcohol and water to give 5.78 g of a light brown solid product. This product could be identified to be 4-trifluoromethylphenyl 4-ethoxycarbonyloxy benzoate from the results of the $^1$H-NMR spectrometric structure analysis shown below. The yield of the reaction product was 88.3% of the theoretical value.

$^1$H-NMR (CDCl$_3$, δ, ppm): 1.42 (t, J=7.0 Hz, 3H, $CH_3CH_2$—O—CO—O—); 4.36 (q, J=7.2 Hz, 2H, $CH_3$ $\overline{CH_2}$—O—CO—O—); 7.37 (m, 4H, aromatic protons); 7.71 $\overline{(d, J}$=8.8 Hz, 2H, aromatic protons); and 8.25 (d, J=8.4 Hz, 2H, aromatic protons)

In the second step, 5.00 g (14.1 mmoles) of the 4-trifluoromethylphenyl ester compound obtained in the first step were dissolved in a mixture of 25 ml of pyridine, 50 ml of acetone and 2.8 ml of 28% ammonia water and the solution was kept overnight under agitation to effect the hydrolysis reaction. After completion of the reaction, the reaction mixture was admixed with methylene chloride and the organic solution was washed first with 1N hydrochloric acid and then with water followed by removal of the solvents by distillation to give a solid product which was purified by recrystallization from a mixture of methyl alcohol and water to give 2.95 g of a slightly brownish, white crystalline material as the product. This product could be identified to be 4-trifluoromethylphenyl 4-hydroxy benzoate from the results of the $^1$H-NMR spectrometric structure analysis shown below. The yield of this reaction product was 74.1% of the theoretical value.

$^1$H-NMR (CDCl$_3$, δ, ppm): 6.91 (d, J=8.8 Hz, 2H, aromatic protons); 7.33 (d, J=8.4 Hz, 2H, aromatic protons); 7.69 (d, J=8.8 Hz, 2H, aromatic protons); and 8.11 (d, J=8.8 Hz, 2H, aromatic protons)

In the third step, 1.00 g (3.54 mmoles) of the 4-trifluoromethylphenyl 4-hydroxybenzoate prepared above was dissolved in a mixture of 0.5 ml (4 mmoles) of triethylamine and 15 ml of acetone with agitation under chilling in an ice bath to prepare a reaction mixture to which 0.60 g (3.5 mmoles) of p-anisoyl chloride was added dropwise over a period of 15 minutes followed by further continued agitation of the reaction mixture overnight in the ice bath as such to effect the esterification reaction. After completion of the reaction, the reaction mixture was admixed with methylene chloride and the organic solution was washed with water and then freed from the solvents by distillation to give a solid material which was purified by recrystallization from a mixture of acetone and water to give 1.29 g of a white crystalline product. This product could be identified to be the desired aromatic ester compound E3-$CF_3$ from the results of the $^1$H-NMR spectrometric structure analysis shown below. The yield of the reaction product was 87.5% of the theoretical value.

$^1$H-NMR (CDCl$_3$, δ, ppm): 3.92 (s, 3H, $\underline{CH_3}$—O—Ph—); 7.01 (d, J=8.0 Hz, 2H, aromatic protons); 7.38 (m, 4H, aromatic protons); 7.72 (d, J=8.0 Hz, 2H, aromatic protons); 8.18 (d, J=8.0 Hz, 2H, aromatic protons); and 8.29 (d, J=8.0 Hz, 2H, aromatic protons)

The wavelength for the absorption maximum $\lambda_{max}$ and the cut-off wavelength $\lambda_{co}$ of the compound E3-CF3 determined from the ultraviolet absorption spectrum of an acetonitrile solution were 263 nm and 295 nm, respectively.

EXAMPLE 5

The aromatic ester compound E2-$NO_2$ was synthesized in the following manner. Thus, a reaction mixture was prepared by dissolving 4.30 g (30.9 mmoles) of 4-nitrophenol and 4.3 ml (31 mmoles) of triethylamine in 15 ml of acetone with agitation under chilling in an ice bath. In the next place, a solution of 5.27 g (30.9 mmoles) of p-anisoyl chloride dissolved in 10 ml of acetone was added dropwise to the reaction mixture over a period of 15 minutes followed by further continued agitation of the mixture kept in the ice bath as such overnight to effect the reaction.

After completion of the reaction, the reaction mixture was admixed with methylene chloride and the organic solution was washed with water and then freed from the solvents by distillation to give a solid product, which was purified by recrystallization from a mixture of methyl alcohol and acetone to give 7.67 g of a light yellow crystalline product. This product could be identified to be the desired aromatic ester compound E2-$NO_2$ from the results of the $^1$H-NMR spectrometric structure analysis shown below. The yield of the reaction product was 90.9% of the theoretical value.

$^1$H-NMR (CDCl$_3$, δ, ppm): 3.91 (s, 3H, $\underline{CH_3}$—O—Ph—); 7.01 (d, J=8.8 Hz, 2H, aromatic protons); $\overline{7.41}$ (d, J=8.8 Hz, 2H, aromatic protons); 8.15 (d, J=8.8 Hz, 2H, aromatic protons); and 8.32 (d, J=9.2 Hz, 2H, aromatic protons)

The wavelength for the absorption maximum $\lambda_{max}$ and the cut-off wavelength $\lambda_{co}$ of the compound E2-$NO_2$ determined from the ultraviolet absorption spectrum of an acetonitrile solution were 275 nm and 380 nm, respectively.

REFERENCE EXAMPLE

A polymer solution containing the inventive aromatic ester compound was prepared by dissolving 0.02 g of the respective aromatic ester compound prepared in each of Examples 1 to 5 described above and 0.18 g of a polymethyl methacrylate resin in 5 ml of chloroform. A glass plate of 1.0 mm thickness was uniformly coated with this polymer solution on a spinner rotating at 500 rpm for 30 seconds followed by drying to form a thin resin film having a thickness of about 500 nm. Molecular dispersion of the aromatic ester compound in the resin film could be assumed as is suggested by the good coincidence between the ultraviolet absorption spectrum of the here prepared resin film and that of the acetonitrile solution of the same compound for each of the inventive aromatic ester compounds.

Each of the thus prepared resin films containing one of the inventive aromatic ester compounds was subjected to a corona poling treatment in an electric field of 5 kV/cm at different temperatures to determine the optimum poling temperature. Further, a resin film after poling at the optimum temperature was subjected to the measurement of SHG (second harmonic generation) by the Maker Fringe method to calculate the second-order non-linear optical coefficient $d_{33}$ according to the conventional method. The Table below shows the thus obtained optimum poling temperature and the value of $d_{33}$ in the unit of $10^{-9}$ esu for each of the aromatic ester compounds.

TABLE

| Compound | Optimum poling temperature, ° C. | Second-order non-linear optical coefficient $d_{33}$, $10^{-9}$ esu |
|---|---|---|
| Example 1: E2—CN | 60–70 | 2.3 |
| Example 2: E3—CN | 80–90 | 3.8 |
| Example 3: E2—CF$_3$ | 70–80 | 2.1 |
| Example 4: E3—CF$_3$ | 80–90 | 3.0 |
| Example 5: E2—NO$_2$ | 70–80 | 2.5 |

What is claimed is:

1. A second-order non-linear optical material which is a film of a polymeric resin containing an aromatic ester compound represented by the general formula

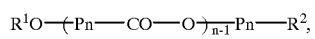

in which Pn is a 1,4-phenylene group, $R^1$ is an alkyl group having 1 to 4 carbon atoms, $R^2$ is a group selected from the group consisting of perfluoroalkyl groups having 1 to 4 carbon atoms, cyano group, nitro group, 2,2-dicyanoethenyl group and methylsulfonyl group and the subscript n is a number of 2, 3 or 4.

2. The second-order non-linear optical material as claimed in claim 1 in which the polymeric resin is a polymethyl methacrylate resin.

* * * * *